(12) United States Patent
Bonde

(10) Patent No.: US 10,086,190 B2
(45) Date of Patent: Oct. 2, 2018

(54) METHODS, TOOLS, AND ASSEMBLIES FOR IMPLANTATION OF MEDICAL LEADS HAVING DISTAL TIP ANCHORS

(71) Applicant: Medtronic, Inc., Minneapolis, MN (US)

(72) Inventor: Eric H. Bonde, Minnetonka, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 773 days.

(21) Appl. No.: 13/658,047

(22) Filed: Oct. 23, 2012

(65) Prior Publication Data

US 2013/0103049 A1    Apr. 25, 2013

Related U.S. Application Data

(60) Provisional application No. 61/551,117, filed on Oct. 25, 2011.

(51) Int. Cl.
*A61N 1/05* (2006.01)
*A61B 17/34* (2006.01)

(52) U.S. Cl.
CPC ............ *A61N 1/05* (2013.01); *A61B 17/3468* (2013.01); *A61N 1/0558* (2013.01); *A61N 1/0504* (2013.01)

(58) Field of Classification Search
CPC ........ A61B 17/3468; A61N 1/05; A61N 1/05; A61N 1/0558; A61N 1/057; A61N 1/059; A61N 1/0539

USPC ................ 606/129, 107, 205–209; 623/6.12; 600/372–385
See application file for complete search history.

(56) References Cited

U.S. PATENT DOCUMENTS

| | | | |
|---|---|---|---|
| 5,344,439 | A | 9/1994 | Otten |
| 2006/0122676 | A1 | 6/2006 | Ko et al. |
| 2008/0103576 | A1 | 5/2008 | Gerber |
| 2008/0208247 | A1 | 8/2008 | Rutten et al. |
| 2010/0030311 | A1* | 2/2010 | Lazeroms et al. ............ 607/119 |

OTHER PUBLICATIONS http://www.thefreedictionary.com/rod.*

* cited by examiner

*Primary Examiner* — Kathleen Holwerda
*Assistant Examiner* — Socrates L Boutsikaris
(74) *Attorney, Agent, or Firm* — Withers & Keys, LLC

(57) ABSTRACT

Medical leads include distal tip anchors that are retained by fixation mechanisms of implantation tools. The fixation mechanism may include a fixed body that has features retaining the distal tip anchor. The fixation mechanism may include a movable body that can apply tension to the distal tip anchor to force the distal tip anchor to be released from the features of the fixed body. The movable body may include an axial portion that is received by an axial hole of the fixed body to allow for axial movement of the movable body to release the distal tip anchor. The fixation mechanism may instead include an elongated flexible body that passes through the distal tip anchor and is attached to the fixed body. Tension applied to the elongated body creates a releasing motion of the distal tip anchor to free the distal tip anchor from the features of the fixed body.

6 Claims, 10 Drawing Sheets

METHODS, TOOLS, AND ASSEMBLIES FOR IMPLANTATION OF MEDICAL LEADS HAVING DISTAL TIP ANCHORS

CROSS-REFERENCE TO RELATED APPLICATIONS

The present application claims priority to U.S. Provisional Patent Application No. 61/551,117, filed Oct. 25, 2011, which application is hereby incorporated by reference as if re-written in its entirety.

TECHNICAL FIELD

Embodiments are related to the implantation of a medical lead. More particularly, embodiments are related to the implantation of a medical lead having a distal tip anchor.

BACKGROUND

Medical leads are implanted in the body of a patient in order to deliver medical therapy. The implantation process varies depending upon the type of medical lead and the particular location within the body where the medical lead is being implanted. In the case of percutaneous leads, the implantation process typically involves inserting an introducer to nearby the stimulation site and then guiding the lead through the introducer and ultimately steering the distal end of the lead to the proper location. For subcutaneous implantation of a percutaneous lead, such as for occipital or peripheral nerve applications, an introducer is used to tunnel subcutaneously to the stimulation site and then the lead is inserted through the introducer. Thus, tunneling to the stimulation site and guiding the lead to the stimulation site is a multi-step process.

Once to the stimulation site, it is desirable to anchor the medical lead in position so that body movement does not result in the medical lead migrating away from the stimulation site. However, for subcutaneous implantation, conventional anchoring may be relatively ineffective or undesirable due to the subcutaneous tissue and location. In some instances, anchors may not be installed and the lead may be directly sutured. In either case, the distal end of the lead at the stimulation site may be subject to migration that hinders the ability to stimulate the intended tissue.

To assist in anchoring the distal end of the lead, a lead with a distal tip anchor may be chosen. While this may be beneficial once implanted, implanting a medical lead with a distal tip anchor may be difficult because the distal tip anchor obstructs the passage of the medical lead through an introducer and/or subcutaneous tissue.

SUMMARY

Embodiments address issues such as these and others by providing methods, tools, and assemblies that provide for implantation of medical leads having distal tip anchors. A tool for implanting the medical lead has a fixation mechanism on a distal end. The distal tip anchor is restrained by the fixation mechanism as the tool tunnels to the stimulation site, thereby delivering the medical lead. Once at the stimulation site, the fixation mechanism releases the distal tip anchor and the tool is removed. The fixation mechanism may include features such as a movable body and/or an elongated body attached at the distal tip of the tool that forces the distal tip anchor free of the fixation mechanism.

Embodiments include a method of preparing a medical lead having a distal tip anchor for implantation. The method involves placing a body of the medical lead into an open area of a tool. The method further involves attaching the distal tip anchor to a fixation mechanism on a distal tip of the tool such that the medical lead is held in a fixed position relative to the tool. The fixation mechanism has a first state and a second state, the first state providing fixation of the medical lead by contact with a feature of a fixed body of the fixation mechanism to maintain the lead in the fixed position and the second state providing release of the medical lead from the fixed position by contact with a movable body of the fixation mechanism. The movable body has an axial portion that engages an axial hole of the fixed body allowing the movable body to move axially relative to the fixed body.

Embodiments provide a method of preparing a medical lead having a distal tip anchor for implantation. The method involves placing a body of the medical lead into an open area of a tool. The method further involves attaching the distal tip anchor to a fixation mechanism on a distal tip of the tool such that the medical lead is held in a fixed position relative to the tool, the fixation mechanism having a fixed body and an elongated flexible body with a distal end attached to a top of the fixed body, the fixation mechanism having a first state and a second state. The first state provides fixation of the medical lead to maintain the lead in the fixed position by having the distal tip anchor restrained by a feature of the fixed body with an elongated flexible body present between the body of the medical lead and a surface of the tool while passing through the distal tip anchor. The second state provides release of the medical lead from the fixed position by the elongated flexible body having an applied tension to impart a releasing motion to the distal tip anchor.

Embodiments provide a medical assembly that includes a medical lead having a lead body including a distal tip anchor and a plurality of electrodes in proximity to the distal tip anchor. The medical assembly also includes a tool having a tool body with an open area and having a distal tip fixation mechanism, the lead body being present within the open area and the distal tip anchor being attached to the distal tip mechanism to provide a fixed position of the lead relative to the tool. The fixation mechanism has a first state and a second state, the first state providing fixation of the medical lead by contact with a feature of a fixed body of the fixation mechanism to maintain the lead in the fixed position and the second state providing release of the medical lead from the fixed position by contact with a movable body of the fixation mechanism. The movable body has an axial portion that engages an axial hole of the fixed body allowing the movable body to move axially relative to the fixed body.

Embodiments provide a medical assembly that includes a medical lead having a lead body including a distal tip anchor and a plurality of electrodes in proximity to the distal tip anchor. The medical assembly further includes a tool having a tool body with an open area and having a distal tip fixation mechanism, the lead body being present within the open area and the distal tip anchor being attached to the distal tip mechanism to provide a fixed position of the lead relative to the tool. The fixation mechanism has a fixed body and an elongated flexible body with a distal end attached to a top of the fixed body, the fixation mechanism having a first state and a second state. The first state provides fixation of the medical lead to maintain the lead in the fixed position by having the distal tip anchor restrained by a feature of the fixed body with an elongated flexible body present between the body of the medical lead and a surface of the tool while passing through the distal tip anchor, and the second state provides release of the medical lead from the fixed position by the elongated flexible body having an applied tension to impart a releasing motion to the distal tip anchor.

Embodiments provide a method of testing stimulation that involves tunneling a distal tip of a tool to a target stimulation site, the tool having a fixation mechanism on the distal tip and having an open area, with a lead body of a medical lead being present within the open area and with a distal tip anchor of the medical lead being attached to the tool by the fixation mechanism, and with at least one distal electrode of the medical lead being exposed from the tool. The method further involves connecting a proximal end of the medical lead to a medical stimulation device, the proximal end having a proximal connector that makes electrical connection with an electrical connector of the medical stimulation device, with a filar electrically connecting the proximal connector to the distal electrode. The method further involves applying stimulation energy from the medical stimulation device to the distal electrode while the medical lead is present within the open area of the tool.

Embodiments provide a medical lead introducer tool that includes a tool body with an open area and a distal tip fixation mechanism present at a distal tip of the tool body. The fixation mechanism has a first state and a second state, the first state providing fixation of the medical lead by contact with a feature of a fixed body of the fixation mechanism to maintain the lead in the fixed position and the second state providing release of the medical lead from the fixed position by contact with a movable body of the fixation mechanism. The movable body has an axial portion that engages an axial hole of the fixed body allowing the movable body to move axially relative to the fixed body.

Embodiments provide a medical lead introducer tool that includes a tool body with an open area and a distal tip fixation mechanism present at a distal tip of the tool body. The fixation mechanism has a fixed body and an elongated flexible body with a distal end attached to a top of the fixed body, the fixation mechanism having a first state and a second state. The first state provides fixation of the medical lead to maintain the lead in the fixed position by having the distal tip anchor restrained by a feature of the fixed body with the elongated flexible body present between the body of the medical lead and a surface of the tool while passing through the distal tip anchor. The second state provides release of the medical lead from the fixed position by the elongated flexible body having an applied tension to impart a releasing motion to the distal tip anchor.

DETAILED DESCRIPTION

Embodiments provide an implantation tool that includes a fixation mechanism for restraining a distal tip anchor of a medical lead during tunneling to a stimulation site. The fixation mechanism may be of various forms. Some embodiments may include a movable body axially engaged with an axial hole of a fixed body to release the distal tip anchor from a retained position when the movable body transitions. Other embodiments may include an elongated flexible body with a distal end attached to a fixed body to release the distal tip anchor from a retained position when tension is applied to the elongated flexible body.

Figure 1:
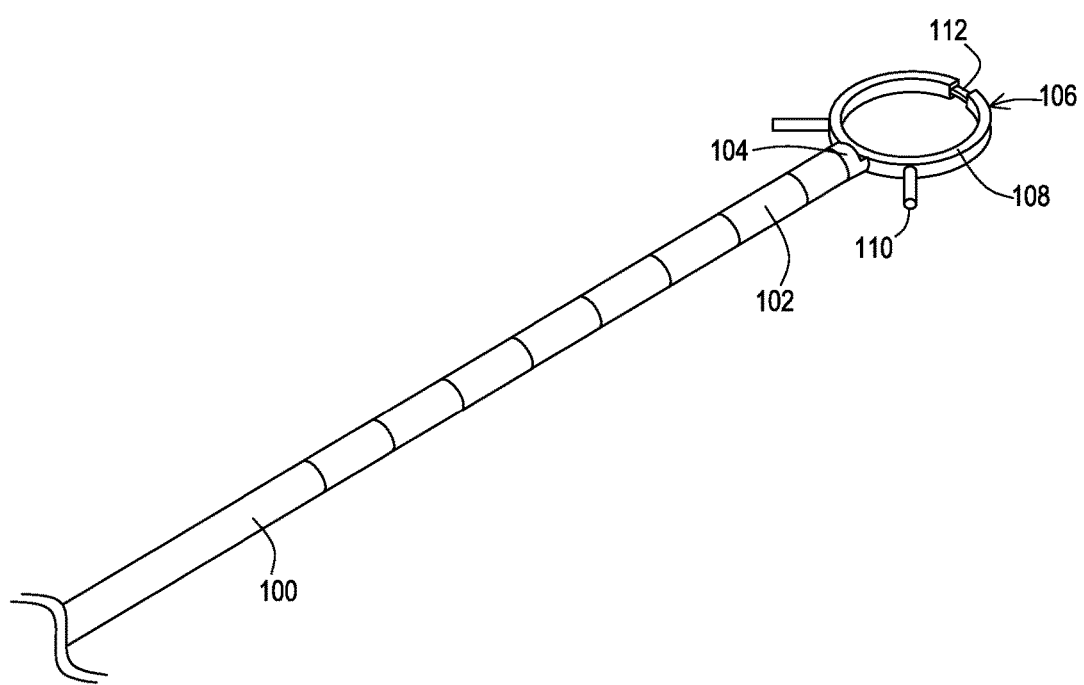
FIG. 1 shows a subcutaneously implantable medical lead having a distal tip anchor.

FIG. 1 shows one example of a lead 100 having a plurality of distal electrodes 102. A distal end 104 of the lead is attached to a distal tip anchor 106. The distal tip anchor 106 includes a body 108 that forms a ring or similar shape. This ringed shape body 108 providing a wider lateral dimension than the lead 100 immediately provides a degree of fixation. Additionally, tissue grows about this body 108 to firmly anchor the distal end 104 in position over time.

The distal anchor 106 may be constructed of a flexible and biocompatible material such as 55D polyurethane. The distal anchor 106 may be formed integrally with the lead body or may be formed separately and then affixed to the distal end 104 with an adhesive.

This example of the distal tip anchor 106 also includes tines 110 that protrude outwardly at an angle relative to the axial direction of the lead 100. These tines 110 provide additional fixation immediately upon implantation.

This embodiment of the distal tip anchor 106 also includes a breakaway notch 112 which is an area of the ringed body 108 that is structurally weaker. The breakaway notch 112 allows the lead 100 to be removed even after tissue has grown through the ringed body 108. By applying axial force in the proximal direction, the breakaway notch 112 will sever and thereby release from the tissue growth.

Figure 2:
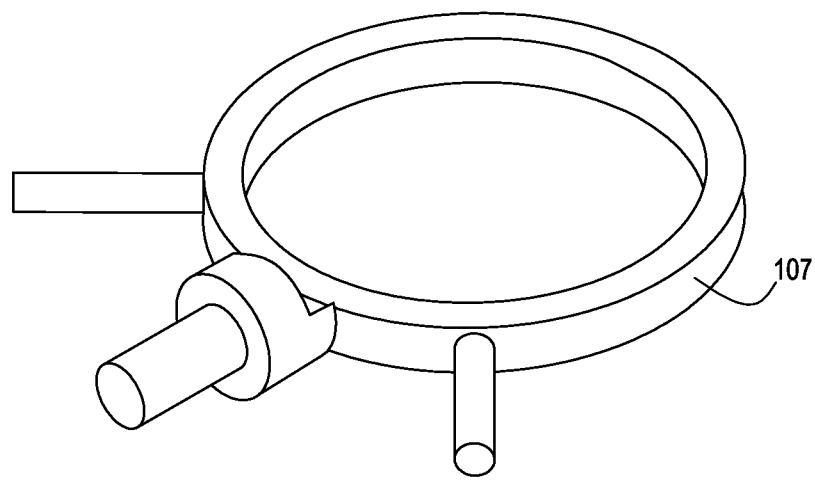
FIG. 2 shows a first alternative distal tip anchor.
Figure 3:
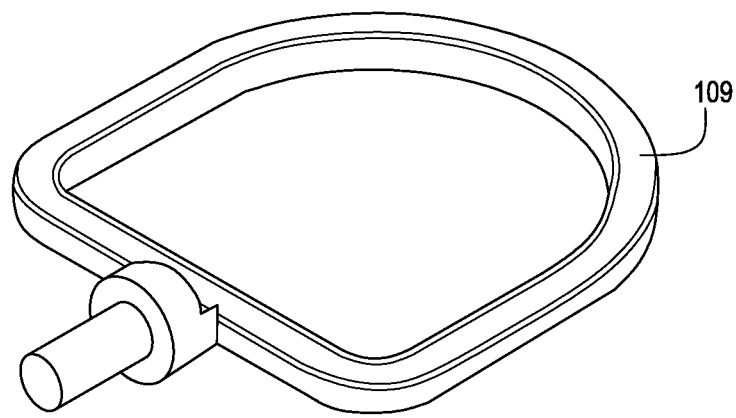
FIG. 3 shows a second alternative distal tip anchor.

FIG. 2 shows one alternative distal anchor 107 prior to being affixed to a lead. In this particular example, the breakaway notch from the example in FIG. 1 is omitted. FIG. 3 shows another alternative distal anchor 109. This distal anchor 109 utilizes a more angular proximal side to provide additional fixation without the use of tines. Furthermore, this example also omits the breakaway notch. However, it will be appreciated that the breakaway notch as well as the tines shown in the example of FIG. 1 may be included for the embodiment of FIG. 3.

Figure 4:
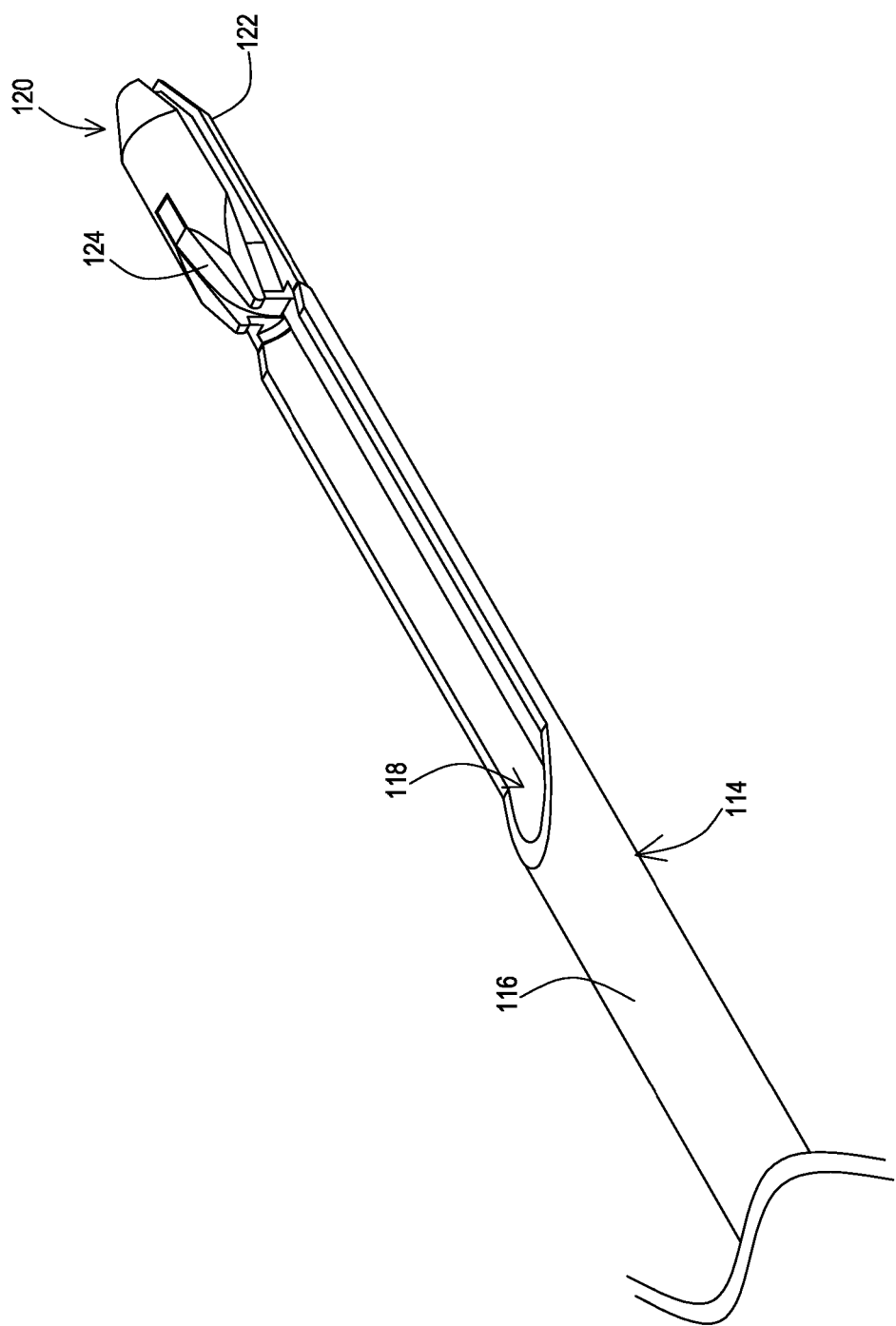
FIG. 4 shows an implantation tool for medical leads having a distal tip anchor.

FIG. 4 shows an implantation tool 114 that may be used to subcutaneously implant the lead 100. The implantation tool 114 includes a tool body 116 that defines an open area 118 near the distal end. In this example, the open area 118 is defined by an aperture of a lumen in conjunction with a trough. Other configurations for the open area 118 may alternatively be used, such as being confined to the tool body lumen and/or may include a series of openings about the circumference of the tool body 116. The relationship of the open area 118 to the distal electrodes of the lead is discussed in more detail below.

The implantation tool 114 also includes a fixation mechanism 120 located at the distal tip. In the example shown in FIG. 4, the fixation mechanism 120 includes a fixed body 122 that is affixed to the tool body 116 and a movable body 124 such as a plunger that is movable with respect to the fixed body 122. The fixed body 122 and movable body 124 interface with the distal tip anchor 106 of the lead 100 to retain and release the distal tip anchor 106 as discussed further below.

The implantation tool 114 may be constructed of a rigid material such as a thin walled biocompatible metal or a glass filled biocompatible polymer. The fixed body 122 and movable body 124 may be constructed of rigid materials such as a biocompatible metal. As shown, the fixed body 122 has a tapered distal end to facilitate the dissection that occurs as the implantation tool 114 is tunneling subcutaneously to the implantation target site.

Figure 5:
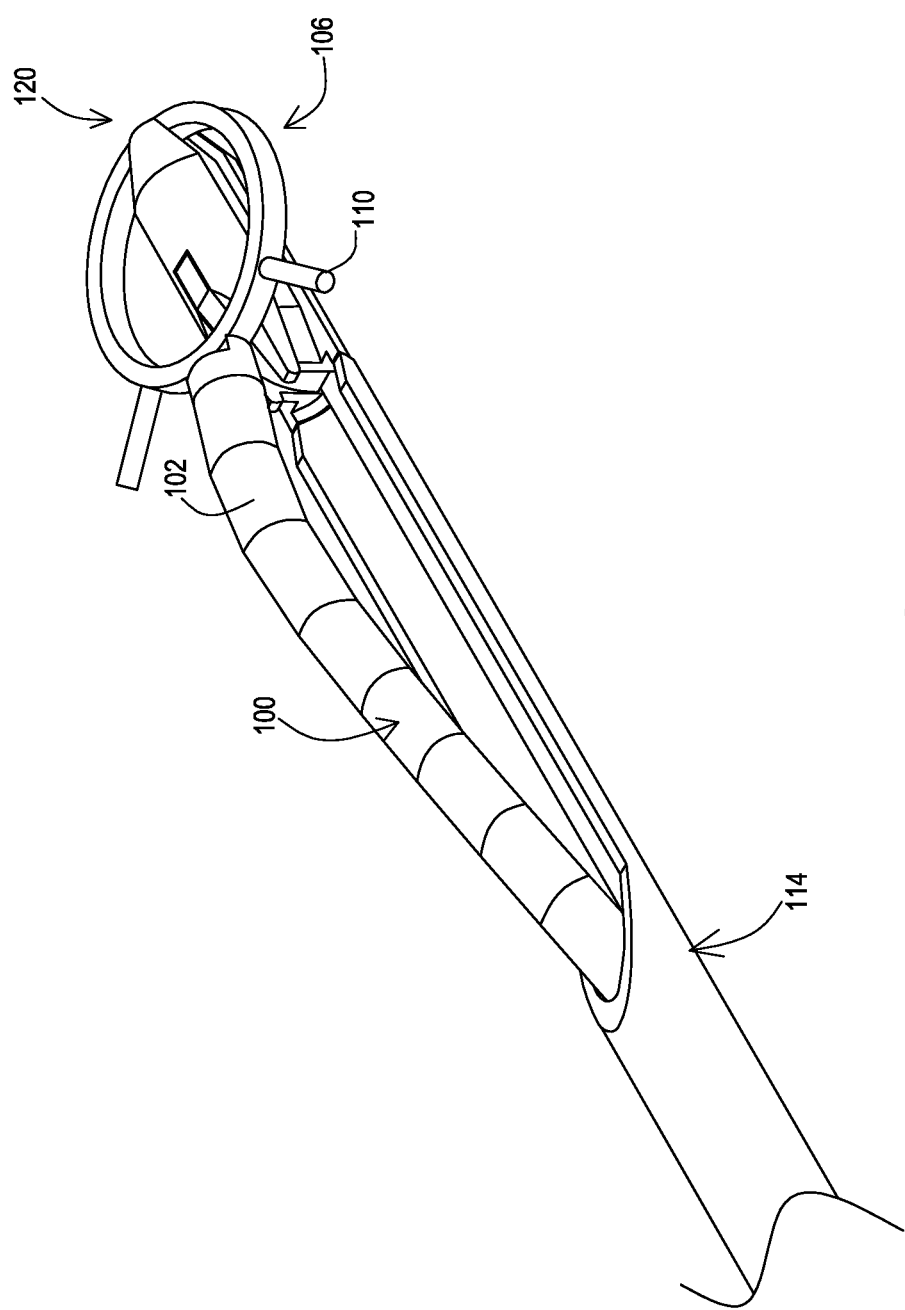
FIG. 5 shows a medical assembly including a medical lead with a distal tip anchor being installed within an implantation tool while the distal tip anchor is yet to be retained.

The lead 100 is installed onto the implantation tool 114 prior to the implantation tool 114 being guided subcutaneously to the implantation target site. Thus, the lead 100 is implanted simultaneously with the introduction of the tool 114 to the target site. In order to install the lead 100 onto the implantation tool 114, the proximal end of the lead 100 is inserted through the open area 118 into the lumen of the tool body 116 until the distal tip anchor 106 reaches the fixation mechanism 120 as shown in FIG. 5.

Figure 6A:
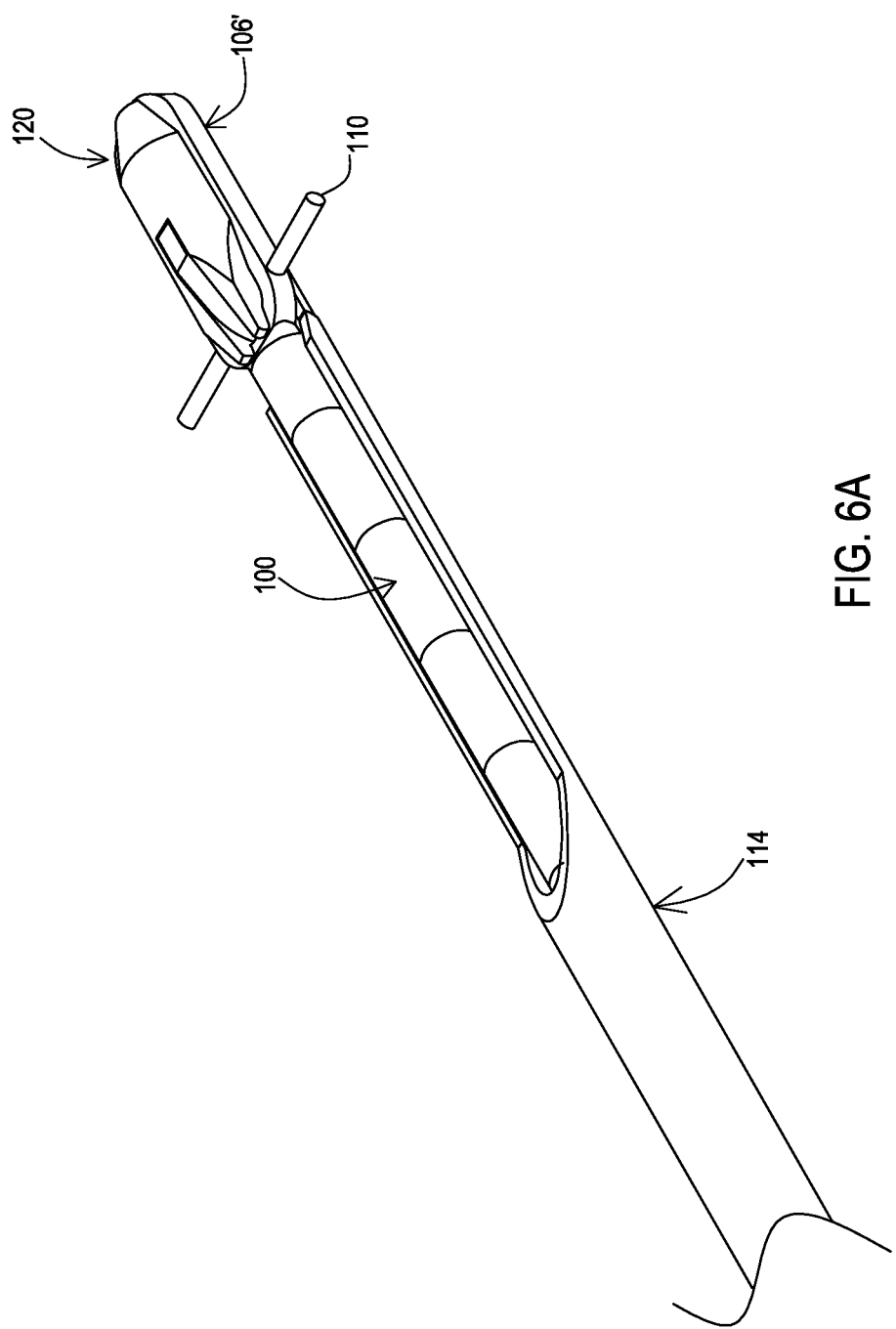
FIG. 6A shows the medical assembly including the medical lead with the distal tip anchor installed within an implantation tool with the distal tip anchor in a retained position.

Once the distal tip anchor 106 is adjacent the fixation mechanism 120, the ringed body 108 is attached to the fixation mechanism 120 to thereby fix the position of the lead 100 within the implantation tool 114. As can be seen in FIG. 6A, features 128 of the fixed body 122 retain the proximal end of the ringed body 108. Furthermore, as shown in FIG. 6A, the distal tip anchor 106 is stretched in the axial dimension when being attached to the fixation mechanism 120 which reduces the lateral dimension of the distal tip anchor 106'. This reduction provides a less restrictive configuration for traversing the subcutaneous pathway to the target site. The tines 110 flex during implantation to further reduce restriction during implantation.

Figure 6B:
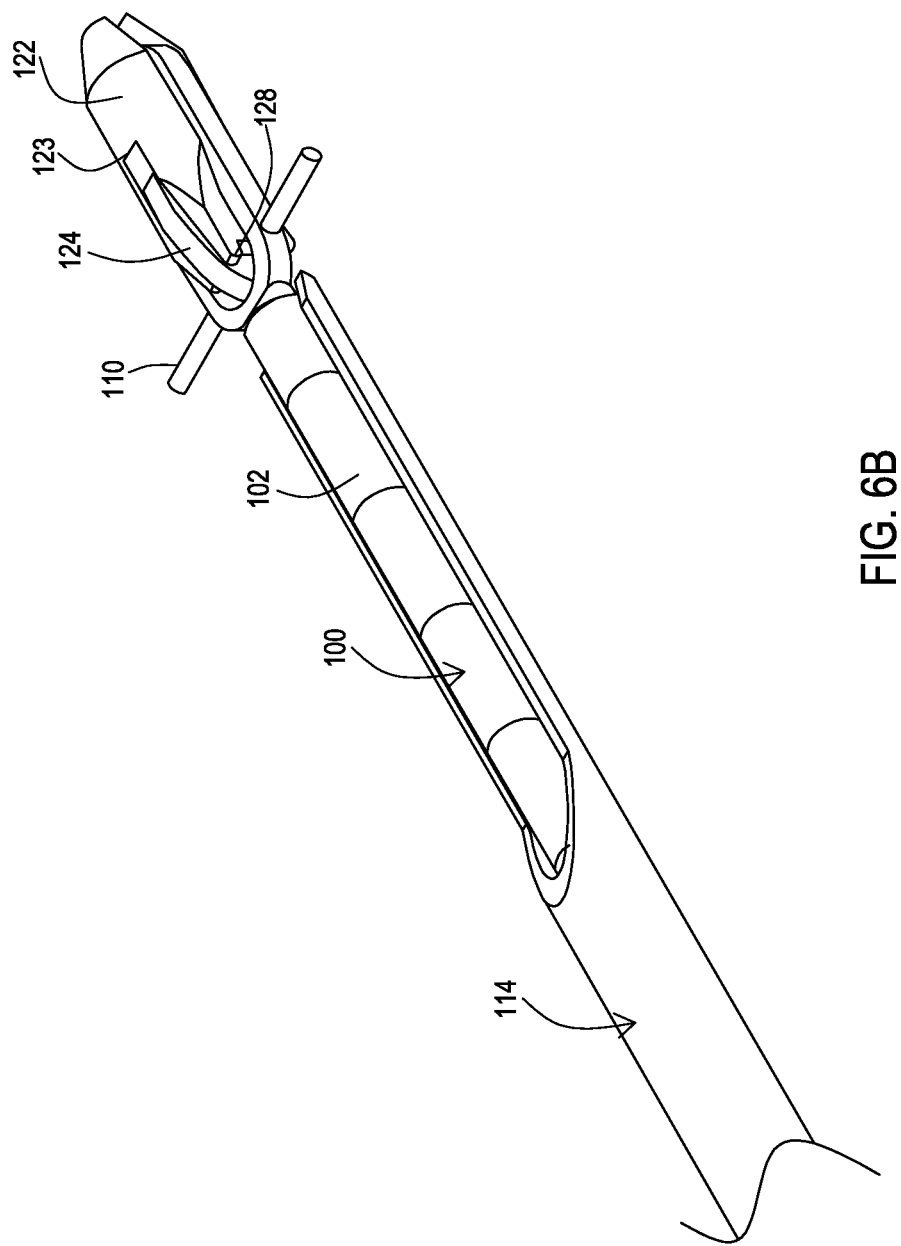
FIG. 6B shows the medical assembly with the distal tip anchor of the medical being released from a fixation mechanism of the implantation tool.

While the distal tip anchor 106' is being retained as shown in FIG. 6A, the distal tip anchor 106' is being released in FIG. 6B. FIG. 6A shows the fixation mechanism 120 in a first state where the movable body 124 rests against a distal abutment 123 formed by the fixed body 122 and therefore is not forcing the ringed body 108 in the proximal direction. FIG. 6B shows the fixation mechanism 120 in a second state where the movable body 124 is forcing the ringed body 108 in the proximal direction, which frees the proximal end of the ringed body 108 from the features 128 of the fixed body 122. The movable body 124 has transitioned away from the distal abutment 123 and the ringed body 108 may then slide upward along the tapered proximal edge of the movable body 124 and ultimately become free of the fixation mechanism 120, thereby returning to the configuration shown in FIG. 5. At this point, the implantation tool 114 may then be retracted with the lead 100 exiting the implantation tool by remaining in the current position with the electrodes 102 at the target site.

Figure 7:
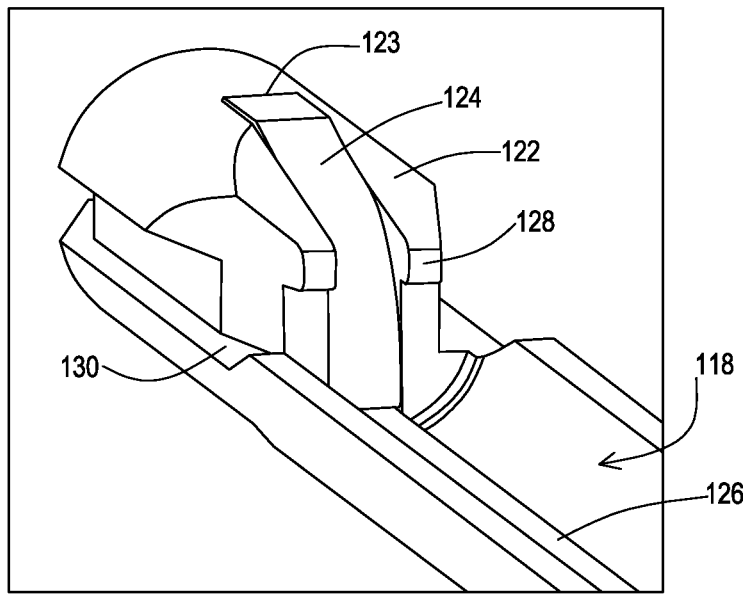
FIG. 7 shows a first view of a first embodiment of the fixation mechanism.

FIG. 7 shows the proximal end of the fixation mechanism 120 in greater detail. Here the relationship of the movable body 124 and the features 128 of the fixed body 122 can be seen. Additionally, a groove 130 is present about the periphery of the fixed body 122 to receive the ringed body 108 of the distal tip anchor 106. The movable body 124 includes a tension inducing item 126 such as a pull ribbon that extends through the lumen of the tool body 106 to the proximal end. The pull ribbon may be constructed from various materials such as stainless steel or other metal suitable for welding to movable body 124.

Figure 8:
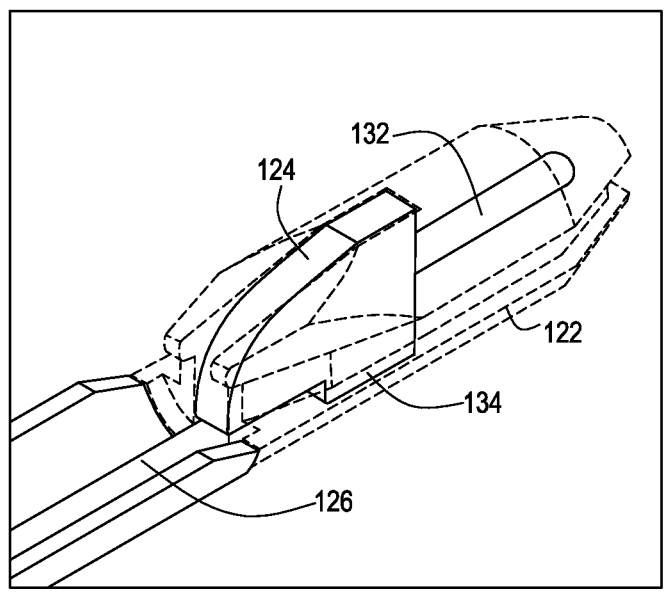
FIG. 8 shows a second view of the first embodiment of the fixation mechanism.

FIG. 8 shows the fixed body 122 in a translucent manner so that the various features of the movable body 124 such as a plunger structure can be seen in relation to the fixed body 122. The movable body 124 includes an axial portion 132 that resides within an axial hole of the fixed body 122. The axial portion 132 within the axial hole restricts the movable body 124 to axial movement relative to the fixed body 122. The movable body 124 of this example also includes a protrusion 134 that resides within an axial slot of the fixed body 122 to further limit the movement.

Figure 10:
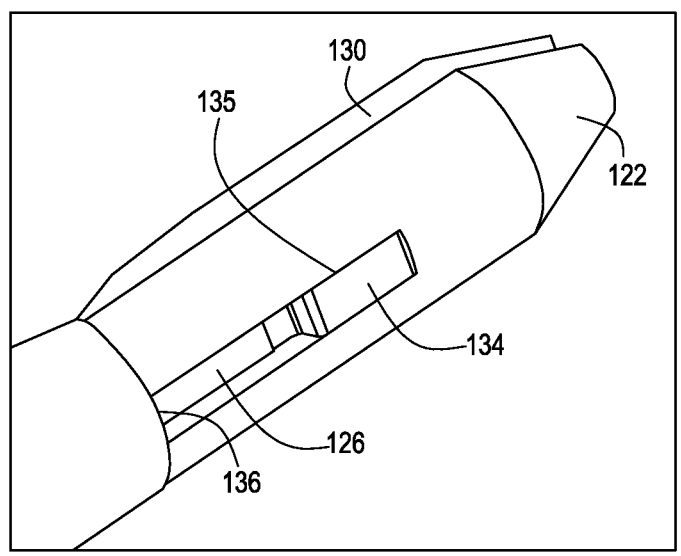
FIG. 10 shows a fourth view of the first embodiment of the fixation mechanism.

As shown in FIG. 10, the fixed body 122 includes an axial slot 135 with an abutment 136 where the protrusion 134 resides within the axial slot 135. The protrusion 134 encounters the abutment 136 when the movable body 124 is being moved proximally to free the ringed body 108 from the fixation mechanism, and the abutment 136 thereby limits the proximal movement of the movable body 124 relative to the fixed body 122. The attachment of the tension inducing item 126 to the movable body 124 is also shown. This attachment may be by a weld or other form of adhesion.

Figure 9:
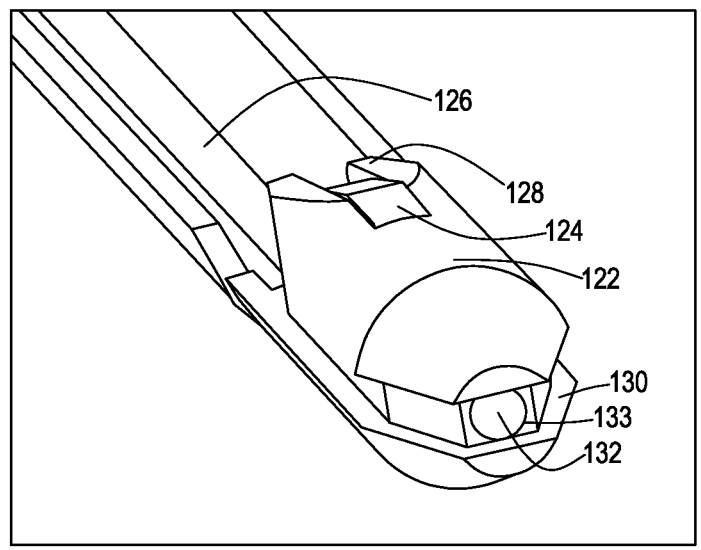
FIG. 9 shows a third view of the first embodiment of the fixation mechanism.

FIG. 9 shows the distal end of the fixation mechanism 120. Here the axial hole 133 of the fixed body 122 can be seen retaining the axial portion 132 of the movable body 124. The distal side of the groove 130 that retains the ringed body 108 can also be seen.

Figure 11:
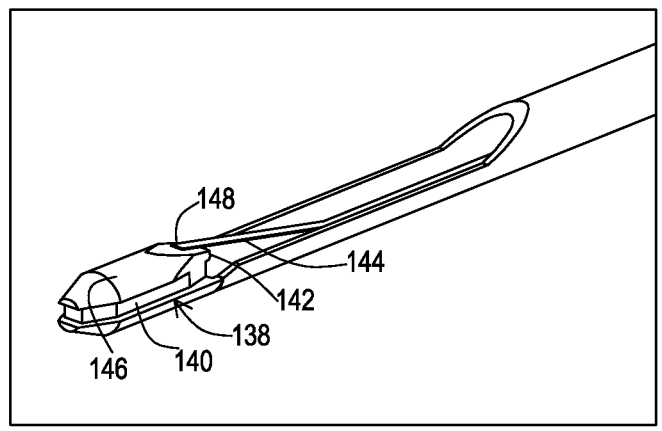
FIG. 11 shows a first view of a second embodiment of the fixation mechanism.

A different embodiment of a fixation mechanism 138 is shown in FIG. 11. In this embodiment, the fixed body 146 includes a groove 140 for retaining the ringed body and also includes features 142 which retain the proximal end of the ringed body 108. However, the fixed body 146 omits the axial hole and axial groove as there is no movable body. Instead, an elongated flexible body 144, such as a pull ribbon as discussed for the previous embodiment, is attached to the fixed body 146 at an attachment point 148. This attachment may be by a weld or other form of adhesion.

For this embodiment, the lead 100 is placed into the lumen of the tool body 116 in the same manner as the previous embodiment. However, the elongated body 144 resides within the tool body lumen between the lead 100 and the tool body 116 and passes through the ringed body 108. In a first state, the elongated body 144 remains untensioned. In a second state, the elongated body 144 is pulled in the proximal direction at the proximal end of the implantation tool 114 to create an applied tension, and the elongated body 144 rises at the distal end and thereby imparts a releasing motion to the ringed body 108. In this example, the releasing motion is rearward and upward due to applied tension to the ringed body 108 which releases the proximal end of the ringed body 108 from the features 142.

Figure 12:
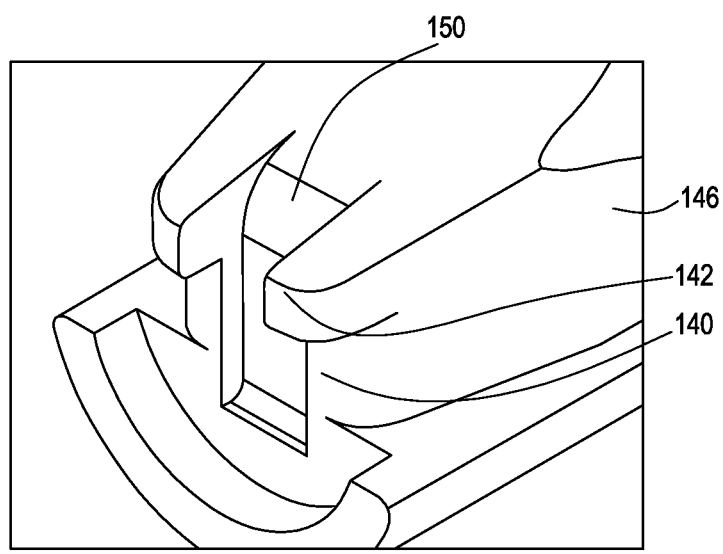
FIG. 12 shows a second view of the second embodiment of the fixation mechanism.

FIG. 12 shows the proximal end of the fixed body 146. The fixed body 146 of this example includes a groove 150 between the features 142 where the elongated body 144 may reside within when passing through the ringed body 108 of the distal tip anchor 106.

Figure 13:
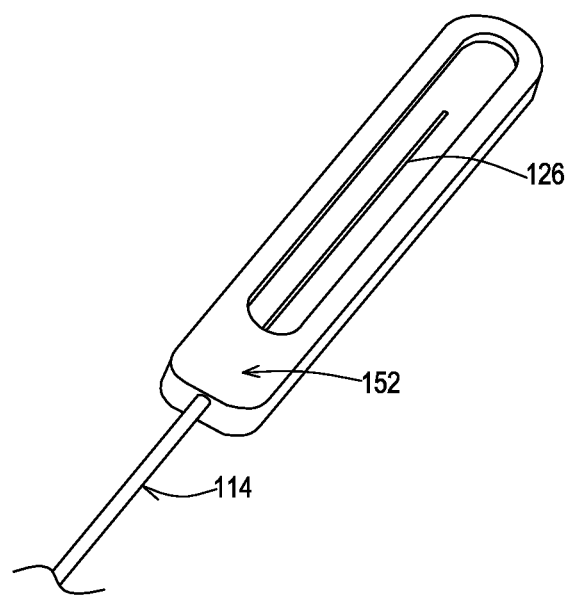
FIG. 13 shows a distal handle of the implantation tool with a first embodiment of a distal end of an elongated body of the fixation mechanism.

FIG. 13 shows a proximal end of an example of the implantation tool 114. A handle 152 is mounted to the proximal end of the tool body 116 and the pull ribbon 126 exits the tool body 116 and the handle 152. Although not shown in FIG. 13, the proximal end of the pull ribbon 126 may be formed into a loop to make the pull ribbon 126 easier to grasp and manipulate.

Figure 14:
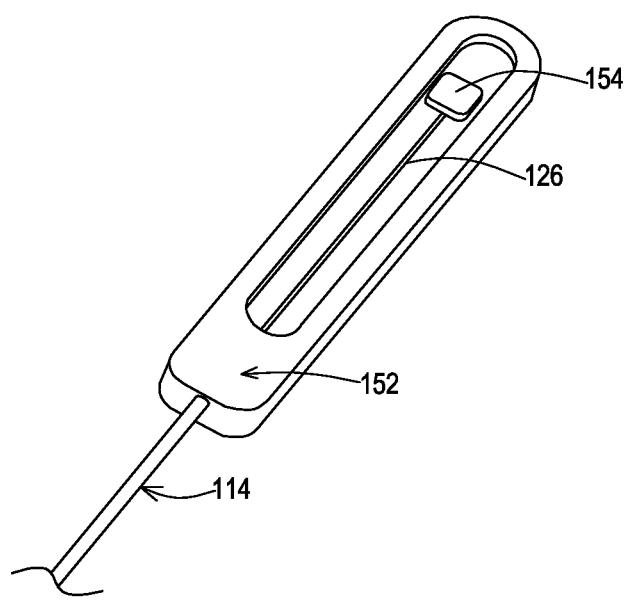
FIG. 14 shows a distal handle of the implantation tool with a second embodiment of a distal end of an elongated body of the fixation mechanism.

FIG. 14 shows a proximal end of another example of the implantation tool 114. In this example, the distal end of the pull ribbon 126 includes a pull tab 154 that makes the pull ribbon 126 easier to grasp and manipulate.

Returning to FIG. 6A, the open area 118 exposes one or more electrodes 102 of the lead 100 to body tissue while the lead 100 remains installed onto the implantation tool 114. Therefore, once the implantation tool 114 has been advanced subcutaneously to the target site, the proximal end of the lead 100 which may be exposed from the area where the handle 152 is located, as in FIG. 13, is connected to the stimulation device. Various mechanisms to ease the connection of the proximal end to the stimulation device may be utilized, such as a twist lock style connector that may be a separate structure or may be integrated into an embodiment of the handle 152 to allow the lead to be locked into the stimulation device with a simple twisting motion.

The electrodes 102 that are exposed may then be activated to test the efficacy of the stimulation with the current electrode positioning. The position may then be repeatedly adjusted as needed by moving the implantation tool 114 prior to releasing the distal tip anchor 106 from the fixation mechanism 120. In embodiments where the tool body is constructed of metal but where the electrode position is to be tested prior to release from the distal tip of the tool 114, at least the interior of the tool body may be made non-conductive so as to avoid short circuits between the electrodes 102. At least the interior of the tool body may be coated with a non-conductive material such as Paralyne or other polymer, may have a hardcoat anodization, or may include a non-conductive sheath surrounding the lead. Once the stimulation is effective, then distal tip anchor 106 may then be released from the fixation mechanism 120 and the implantation tool 114 may be removed while the lead 100 remains in place.

While embodiments have been particularly shown and described, it will be understood by those skilled in the art that various other changes in the form and details may be made therein without departing from the spirit and scope of the invention.

What is claimed is:

1. A medical assembly, comprising:

a medical lead having a lead body including a distal tip anchor and a plurality of electrodes in proximity to the distal tip anchor; and a tool having a tool body with an open area and having a distal tip fixation mechanism, the lead body being present within the open area and extending in an axial direction and the distal tip anchor being attached to the distal tip fixation mechanism to provide a fixed position of the medical lead relative to the tool, the distal tip fixation mechanism having a first state and a second state, the first state providing fixation of the medical lead by contact with a feature of a fixed body of the distal tip fixation mechanism to maintain the medical lead in the fixed position and the second state providing release of the medical lead from the fixed position by contact with a movable body of the distal tip fixation mechanism, the movable body having a body portion and having an axial portion that comprises a cylinder that engages a cylindrical axial hole of the fixed body allowing the entire movable body to move linearly a same distance in the axial direction relative to the fixed body, the cylinder having a longitudinal axis that is parallel to a longitudinal axis of the tool body, the cylinder extending from the body portion, the cylindrical axial hole having a longitudinal axis that is parallel to the longitudinal axis of the tool body.

2. The medical assembly of claim 1, wherein the body portion of the movable body of the distal tip fixation mechanism comprises a plunger connected to a distal end of a pull ribbon.

3. The medical assembly of claim 2, wherein the plunger moves axially in response to force applied to a proximal end of the pull ribbon to contact and move at least a portion of the distal tip anchor so as to release the distal tip anchor from the feature of the fixed body.

4. The medical assembly of claim 2, wherein the fixed body includes an axial slot and wherein the plunger resides at least partially within the axial slot.

5. The medical assembly of claim 4, wherein an abutment at an end of the axial slot contacts the plunger to limit axial movement of the plunger.

6. The medical assembly of claim 1, wherein the feature of the fixed body contacts a proximal region of the distal tip anchor.

* * * * *